US008883692B2

(12) United States Patent
Lee et al.

(10) Patent No.: US 8,883,692 B2
(45) Date of Patent: Nov. 11, 2014

(54) METHOD FOR CELL SURFACE DISPLAYING OF TARGET PROTEINS USING *BACILLUS ANTHRACIS* EXOSPORIUM

(75) Inventors: Sang Yup Lee, Daejeon (KR); Tae Jung Park, Daejeon (KR); Nam Su Heo, Daejeon (KR); Jong Hyun Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 1746 days.

(21) Appl. No.: 12/159,933

(22) PCT Filed: Dec. 29, 2006

(86) PCT No.: PCT/KR2006/005886
§ 371 (c)(1),
(2), (4) Date: Feb. 26, 2009

(87) PCT Pub. No.: WO2007/078127
PCT Pub. Date: Jul. 12, 2007

(65) Prior Publication Data
US 2009/0298706 A1  Dec. 3, 2009

(30) Foreign Application Priority Data
Jan. 2, 2006  (KR) .................. 10-2006-0000187

(51) Int. Cl.
*C40B 40/10*    (2006.01)
*C12P 21/02*    (2006.01)
*C07K 16/00*    (2006.01)
*C07K 14/32*    (2006.01)
*C12N 15/70*    (2006.01)

(52) U.S. Cl.
CPC ............... *C07K 14/32* (2013.01); *C12P 21/02* (2013.01); *C07K 16/00* (2013.01); *C07K 2317/622* (2013.01); *C12N 15/70* (2013.01); *C07K 2319/00* (2013.01)
USPC ........................................................ 506/18

(58) Field of Classification Search
None
See application file for complete search history.

(56) References Cited

U.S. PATENT DOCUMENTS

| 5,114,674 A | 5/1992 | Stanbro et al. |
| 5,807,754 A | 9/1998 | Zambias et al. |

(Continued)

FOREIGN PATENT DOCUMENTS

| EP | 0818467 A3 | 4/1998 |
| WO | 9635953 A1 | 11/1996 |

(Continued)

OTHER PUBLICATIONS

Choi et al. (Feb. 2005) Journal of Microbiology and Biotechnology vol. 15 pp. 141 to 146.*

(Continued)

*Primary Examiner* — Christian Boesen
(74) *Attorney, Agent, or Firm* — Tristan A. Fuierer; Andrew D. Gerschutz; Moore & Van Allen, PLLC

(57) ABSTRACT

The present invention relates to a method for expressing a target protein on the surface of a microorganism using *Bacillus anthracis* exosporium protein. More particularly, to an expression vector constructed such that it comprises bclA gene encoding *Bacillus anthracis* exosporium protein BclA or fragments thereof as a cell surface anchoring motif and the target protein can be expressed on the surface of a cell in a form fused with BclA or a fragment thereof when the gene encoding the target protein is expressed in a host cell, as well as, a method for expressing a target protein on the surface of a microorganism using the vector. The expression vector according to the present invention is capable of effectively expressing a target protein or a peptide on the cell surface using BclA, *Bacillus anthracis* exosporium protein as a cell surface anchoring motif, and since a target protein can be stably expressed on the cell surface in large amounts by culturing a microorganism transformed with the expression vector, thus making it possible to effectively use for the various purposes of recombinant live vaccines, whole cells absorbents, whole cell bioconversion and the like.

14 Claims, 9 Drawing Sheets

Ptac  BA-N        BA-RD                BA-C        Protein

(56) References Cited

U.S. PATENT DOCUMENTS

| | | | | |
|---|---|---|---|---|
| 8,030,064 | B2* | 10/2011 | Lee et al. | .............. 435/320.1 |
| 2004/0180348 | A1 | 9/2004 | Pan et al. | |

FOREIGN PATENT DOCUMENTS

| | | |
|---|---|---|
| WO | 9742507 A1 | 11/1997 |
| WO | 0054046 A2 | 9/2000 |
| WO | 0061806 A2 | 10/2000 |
| WO | 02/055561 A1 | 7/2002 |
| WO | 2005028654 A1 | 3/2005 |

OTHER PUBLICATIONS

Agterberg, Marja, et al., "Outer-membrane PhoE protein of *Escherichia coli* K-12 as an exposure vector: possibilities and limitations", Gene, 88(1): 37-45 (1990).

Cadwell, R C, et al., "Randomization of genes by PCR mutagenesis", PCR Methods Appl., 2:28-33 (1992) (abstract). Abstract only.

Pozzi, G., et al., "Delivery and expression of a heterologous antigen on the surface of streptococci", Infection and Immunity, 60(5):1902-1907 (1992).

Nguyen, Thien Ngoc, et al., "Cell-surface display of heterologous epitopes on *Staphylococcus xylosus* as a potential delivery system for oral vaccination", Gene, 128(1):89-94 (1993).

Francisco, J. A., et al., "Production and fluorescence-activiated cell sorting of . . .", PNAS USA, 90(22):10444-10448 (1993).

Steidler, L., et al., "Pap pili as a vector system for surface exposition of an immunoglobulin G-binding domain of protein A of *Staphylococcus aureus* in *Escherichia coli*.", J. Bacteriol., 175(23):7639-7643 (1993).

Stemmer, Willem P.C., "Rapid evolution of a protein in vitro by DNA shuffling", Nature, 370:389-391 (Aug. 4, 1994).

Pallesen, L., et al., "Chimeric FimH adhesin of type 1 fimbriae: a bacterial surface display system for heterologous sequences", Microbiology, 141:2839-2848 (1995).

Gunneriusson, E., et al., "Surface display of a functional single-chain Fv antibody on staphylococci", J. Bacteriol., 178(5):1341-1346 (1996).

Strauss, Andreas, et al., "In vivo immobilization of enzymatically active polypeptides on the cell surface of *Staphylococcus carnosus*", Molecular Microbiology, 21(3):491-500 (1996).

Richins, Richard D., et al., "Biodegradation of organophosphorus pesticides by surface-expressed organophosphorus hydrolase", Nature Biotechnology, 15:984-987 (1997).

Stahl, Stephan., et al., Trends in Biotechnology, 15(5):185-192 (May 1997).

Georgiou, George, et al., "Display of heterologous proteins on the surface of microorganisms: From the screening of combinatorial libraries to live recombinant vaccines", Nature Biotechnology, 15:29-34 (1997).

Zhao, Huimin, et al., "Molecular evolution by staggered extension process (StEP) in vitro recombination", Nature Biotechnology, 16:258-261 (1998).

Shao, Z., et al., Random-priming in vitro recombination: an effective tool for directed evolution, Nucleic Acids Res., 26(2):681-683 (1998).

Sousa, Carolina, et al., "Metalloadsorption by *Escherichia coli* Cells Displaying Yeast and Mammalian Metallothioneins Anchored to the Outer Membrane Protein LamB", Journal of Bacteriology, 180(9):2280-2284 (May 1998).

Jung, Heung-Chae, et al., "Surface display of *Zymomonas mobilis* levansucrase by using the ice-nucleation protein of *Pseudomonas syringae*", Nature Biotechnology, 16:576-580 (1998).

Park, Si Jae, et al., "Efficient recovery of secretory recombinant proteins from protease negative mutant *Escherichia coli* strains", Biotechnology Techniques, 12(11):815-818 (Nov. 1998).

Ness, Jon E., et al., "DNA shuffling of subgenomic sequences of subtilisin", Nature Biotechnology, 17:893-896 (1999).

Lutz, Stefan, et al., "Homology-independent protein engineering", Current Opinion in Biotechnology, 11(4): 319-324 (2000).

Sylvestre, Patricia, et al., "A collagen-like surface glycoprotein is a structural component of the *Bacillus anthracis* exosporium", Molecular Microbiology, 45(1):169-178 (2002).

Lee, Sang Yup, et al., "Microbial cell-surface display", Trends in Biotechnology, 21(1):45-52 (2003).

Sylvestre, Patricia, et al., "Polymorphism in the Collagen-Like Region of the *Bacillus anthracis* BclA Protein Leads to Variation in Exosporium Filament Length", Journal of Bacteriology, 185(5):1555-1563 (2003).

Lee, Seung Hwan, et al, "Display of Bacterial Lipase on the *Escherichia coli* Cell Surface by Using FadL as an Anchoring Motif and Use of the Enzyme in Enantioselective Biocatalysis", Applied and Environmental Microbiology, 70 (9):5074-5080 (2004).

Lee, Seung Hwan, et al, "Cell Surface Display of Lipase in *Pseudomonas putida* KT2442 Using OprF as an Anchoring Motif and Its Biocatalytic Applications", Applied and Environmental Microbiology, 71(12):8581-8586 (2005).

Charbit, A. et al., "Versatility of a vector for expressing foreign polypeptides at the surface of Gram-negative bacteria", Gene, 70:181-189 (1988).

Sambrook, J., et al., Molecular Cloning: A Laboratory Manual (Second Edition), Cold Spring Harbor, NY, 1989 (abstract).

Georgiou, George, "Analysis of large libraries of protein mutants using flow cytometry," Adv. Protein Chem. 55: 293-315, 293 (2001).

Todd, S.J., Genes of *Bacillus cereus* and *Bacillus anthracis* encoding proteins of the exosporium, Journal of Bacteriology, vol. 185(11), pp. 3373-3378 (Jun. 2003).

Isticato, R., et al., Surface display of recombinant protein on *Bacillus subtilis* spores, Journal of Bacteriology, vol. 183(21), pp. 6294-6301 (Nov. 2001).

* cited by examiner

SEQUENCE LISTING

```
<160> NUMBER OF SEQ ID NOS: 12

<210> SEQ ID NO 1
<211> LENGTH: 83
<212> TYPE: DNA
<213> ORGANISM: Bacillus anthracis

<400> SEQUENCE: 1
atgcaccacc accaccaca cgcatttgac cctaatcttg taggacctac attaccaccg      60
ataccaccat ttacccttcc tac                                            83

<210> SEQ ID NO 2
<211> LENGTH: 552
<212> TYPE: DNA
<213> ORGANISM: Bacillus anthracis

<400> SEQUENCE: 2
atgcaccacc accaccaca ctcaaataat aattattcaa atggattaaa ccccgatgaa      60
tctttatcag ctagtgcatt tgaccctaat cttgtaggac tacattacc accgatacca     120 ccatttaccc ttcctaccgg gccatccgga ctaggacttc cagcaggact atatgcattt    180
aactccggtg ggatttcttt agatttagga attaatgatc cagtaccatt taatactgtt    240
ggatctcagt ttggtacagc aatttctcaa ttagatgctg atactttcgt aattagtgaa    300
actggattct ataaaattac tgttatcgct aatactgcaa cagcaagtgt attaggaggt    360
cttacaatcc aagtgaatgg agtacctgta ccaggtactg gatcaagttt gatttcactc    420
ggagcaccta tcgttattca agcaattacg caaattacga caactccatc attagttgaa    480
gtaattgtta cagggcttgg actatcacta gctcttggca cgagtgcatc cattattatt    540
gaaaaagttg ct                                                        552

<210> SEQ ID NO 3
<211> LENGTH: 777
<212> TYPE: DNA
<213> ORGANISM: Bacillus anthracis

<400> SEQUENCE: 3
atgcaccacc accaccaca ctcaaataat aattattcaa atggattaaa ccccgatgaa      60
tctttatcag ctagtgcatt tgaccctaat cttgtaggac tacattacc accgatacca     120 ccatttaccc ttcctaccgg accaactggg ccgactggac cgactgggcc gactgggcca    180
actggaccaa ctgggccgac tgggccaact ggaccaactg gaccaactgg gccaactgga    240
ccaactgggc caactgggcc aactggagac actggtacta ctggaccaac tgggccaact    300
ggaccaactg gaccaactgg gccaactggt gctaccggac tgactggacc gactggaccg    360
actgggccat ccggactagg acttccagca ggactatatg catttaactc cggtgggatt    420
tctttagatt taggaattaa tgatccagta ccatttaata ctgttggatc tcagtttggt    480
acagcaattt ctcaattaga tgctgatact ttcgtaatta gtgaaactgg attctataaa    540
attactgtta tcgctaatac tgcaacagca agtgtattag gaggtcttac aatccaagtg    600
```

-continued

```
aatggagtac ctgtaccagg tactggatca agtttgattt cactcggagc acctatcgtt    660
attcaagcaa ttacgcaaat tacgacaact ccatcattag ttgaagtaat tgttacaggg    720
cttggactat cactagctct tggcacgagt gcatccatta ttattgaaaa agttgct       777
```

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4

```
ggaattcatg tcaaataata attattc                                         27
```

<210> SEQ ID NO 5
<211> LENGTH: 43
<212> TYPE: DNA
<213> ORGANISM: Artificial
<220> FEATURE:
<223> OTHER INFORMATION: primer

<400> SEQUENCE: 5

```
cgtctagact cgaggctagc cccgggagca acttttcaa taa                        43
```

<210> SEQ ID NO 6
<211> LENGTH: 44
<212> TYPE: DNA
<213> ORGANISM: Artificial
<220> FEATURE:
<223> OTHER INFORMATION: primer

<400> SEQUENCE: 6

```
agtctagact cgaggctagc cccgggggta ggaagggtaa atgg                      44
```

<210> SEQ ID NO 7
<211> LENGTH: 36
<212> TYPE: DNA
<213> ORGANISM: Artificial
<220> FEATURE:
<223> OTHER INFORMATION: primer

<400> SEQUENCE: 7

```
cctagtccgg atggcccggt aggaagggta aatggt                               36
```

<210> SEQ ID NO 8
<211> LENGTH: 36
<212> TYPE: DNA
<213> ORGANISM: Artificial
<220> FEATURE:
<223> OTHER INFORMATION: primer

<400> SEQUENCE: 8

```
accatttacc cttcctaccg ggccatccgg actagg                               36
```

<210> SEQ ID NO 9
<211> LENGTH: 28
<212> TYPE: DNA
<213> ORGANISM: Artificial
<220> FEATURE:
<223> OTHER INFORMATION: primer

<400> SEQUENCE: 9

```
tttacccggg tcgactgagg agtctgga                                        28
```

```
<210> SEQ ID NO 10
<211> LENGTH: 33
<212> TYPE: DNA
<213> ORGANISM: Artificial
<220> FEATURE:
<223> OTHER INFORMATION: primer

<400> SEQUENCE: 10
ctagctagcc tcgagttacg gcttcacctt ggt                                33

<210> SEQ ID NO 11
<211> LENGTH: 27
<212> TYPE: DNA
<213> ORGANISM: Artificial
<220> FEATURE:
<223> OTHER INFORMATION: primer

<400> SEQUENCE: 11
atagctagcg cggcttcgcg agccaat                                       27

<210> SEQ ID NO 12
<211> LENGTH: 28
<212> TYPE: DNA
<213> ORGANISM: Artificial
<220> FEATURE:
<223> OTHER INFORMATION: primer

<400> SEQUENCE: 12
tacaagcttt taaggccgca aactcgca                                      28
```

METHOD FOR CELL SURFACE DISPLAYING OF TARGET PROTEINS USING *BACILLUS ANTHRACIS* EXOSPORIUM

CROSS-REFERENCE TO RELATED APPLICATIONS

This application is filed under the provisions of 35 U.S.C. §371 and claims the priority of International Patent Application No. PCT/KR2006/005886 filed on 29 Dec. 2006 entitled "Method for Cell Surface Displaying of Target Proteins Using *Bacillus Anthracis* Exosporium" in the name of Sang Yup Lee, et al., which claims priority of Korean Patent Application No. 10-2006-0000187 filed on 2 Jan. 2006, both of which are hereby incorporated by reference herein in their entirety.

TECHNICAL FIELD

The present invention relates to a method for expressing a target protein on the surface of a microorganism using *Bacillus anthracis* exosporium protein. More particularly, to an expression vector constructed, such that it comprises bclA gene encoding *Bacillus anthracis* exosporium protein BclA or fragments thereof as a cell surface anchoring motif, and the target protein can be expressed on the surface of a cell in a form fused with BclA or fragments thereof when the gene encoding the target protein is expressed in a host cell, as well as, a method for expressing a target protein on the surface of a microorganism using the vector.

BACKGROUND ART

Bacteria have been playing an important role in development of biotechnology. Especially, since the structure of DNA double helix was discovered by James Watson and Francis Crick, DNA manipulation techniques of microorganisms have been applied to produce a variety of useful materials, and thus, it has become possible to use microorganisms in wide area of industrial applications due to DNA manipulation techniques and techniques for efficiently producing various useful materials have been developed together with the DNA manipulation techniques. Recently, biotechnology, which started with simple protein production, has broadened its application area in various fields.

Among techniques newly introduced based on the remarkable development of biotechnology, there is a cell surface display technique based on a basic knowledge of Molecular biology and a technique of secretion and expression of proteins. Cell surface display is a technique in which proteins or peptides are fused with a proper cell surface anchoring motif to express on the surface of Gram-positive and Gram-negative bacteria, fungus, yeast and animal cells (Lee, S. Y. et al., *Trends Biotechnol.*, 21:4552, 2003). The first cell surface display technique, in which peptides or small proteins are fused with pIII of filamentous phage and named surface-expression system, was developed by George P. Smith in the mid-1980s. Since then, a new way of cell surface display in which desired proteins are stably expressed on the surface of a microorganism was brought to the lime light, as many studies on secretion mechanism in microorganisms are being conducted.

In prior art, studies on the expression of foreign proteins on the surface of phage was conducted because the surface of phage is simpler than that of bacteria. Cell surface display using phages was used in the screening of antibodies, epitopes, high-affinity ligands, etc, but it has a disadvantage in that the size of a protein, which can be expressed on the surface of phage, is relatively limited (Georgiou, G. et al., *Nat. Biotechnol.*, 15:29, 1997). Therefore, as one of the alternatives, cell surface display techniques were developed, in which target proteins are stably expressed on the surface of a microorganism, using surface proteins of microorganisms such as bacteria or yeasts.

Meanwhile, Gram-negative bacteria have a very unique membrane structure consisting of inner cell membrane, periplasmic space, and outer cell membrane. In order to express a foreign protein on the surface of a bacterium, such as *E. coli* having the above mentioned membrane structure, a cell surface anchoring motif, capable of stably and efficiently deliver the foreign protein to be expressed to the surface of a cell, is required. In order to express a foreign protein on the surface of a cell using surface proteins of bacteria, the foreign protein is fused with a proper surface protein at the genomic level to biosynthesize a fusion protein, and the obtained fusion protein should pass through an intracellular membrane to attach on the surface of a cell and maintained. For this, a surface protein having the following properties should be selected and used as a cell surface anchoring motif, the properties are as follows.

The surface protein has a very efficient secretion signal sequence helping a foreign protein to pass through an inner cell membrane in order to deliver it to the surface of a cell, and a targeting signal helping the foreign protein to be stably attached on an outer cell membrane surface, and at the same time, it is capable of delivering a large size of foreign proteins and stably expressing a large amount of the foreign proteins. Cell surface anchoring motifs used until now in *E. coli* were proteins present on the outer membrane such as LamB, PhoE (Agterberg, M. et al., *Gene*, 88:37, 1990), OmpA and so on.

However, when the above mentioned proteins are used, it is advantageous in that a foreign protein can be inserted into a loop protruding form the surface of a cell to be successfully expressed on the surface of a cell, but is has a disadvantage in that the size of the foreign protein which can be inserted, is limited with respect to its structure (Georgiou, G. et al., *Nat. Biotechnol.*, 15:29, 1997).

Also, since the C-terminal end and the N-terminal end of the inserted foreign proteins need to be close three-dimensionally, when both ends are distanced, the both ends need to be genetically engineered to be located closely to one another using a binding peptide. In fact, in the case of LamB or PhoE, when a foreign protein having more than 50-60 amino acids was inserted, a stable membrane protein cannot be formed due to structural limitation (Stahl, S. et al., *Trends Biotechnol*, 15:185, 1997).

When a target protein is fused with a selected surface anchoring motif to express on the surface of a cell, until now, three general fusion methods have been used for the expression on the surface of a cell. The methods are as follows; A method in which a foreign protein to be expressed is fused with the C-terminal end of a surface anchoring motif or a foreign protein to be expressed is fused directly with a surface anchoring motif after deleting the C-terminal end of the surface anchoring motif (C-terminal deletion fusion). INP using levansurase for bioconversion (Jung et al., *Nat. Biotechnol.*, 16:5142, 1999), an outer cell membrane protein C (OmpC) surface-expressing polyhistidine (Xu and Lee, *Appl. Environ. Microbiol.*, 65:5142, 1999), FadL used in reactions exhibiting enantioselectivity of lipase ((Lee et al., *Appl. Environ. Microbiol.*, 70:5074, 2004) and OprF (Lee et al., *Appl. Environ. Microbiol.*, 71:8581, 2005) can be used in this method.

On the contrary to the above method, a method in which a target protein to be expressed is fused with the N-terminal end of a surface anchoring motif. Gram-positive bacteria such as *Staphylococcus aureus* protein A (Gunneriusson, E. et al., *J. Bacteriol*, 178:1341, 1996), fibronectin binding protein B of *Staphylococcus aureus* (Stasuss, A. et al., *Mol. Microbiol.*, 21:491, 1996), fibrillar M protein of *Staphylococcus pyogenes* (Pozzi, G. et al., *Infect. Immun.*, 60:1902, 1992) can be used in this method. Gram-negative bacteria, for instance, *E. coli* cannot be used in this method.

And, sandwich fusion method in which a foreign protein to be expressed on the surface of a cell is fused between the proteins used as a surface anchoring motif. Various proteins, such as PhoE (Agterverg, M. et al., *Gene*, 88:37, 1990), FimH (Pallesen, L., *Microbiology*, 141:2839, 1995), and PapA (Steidler, L. et al., *J. Bacteriol.*, 175:7639, 1993) are used to express the target protein on the surface of *E. coli*. But this method could not overcome disadvantages that foreign proteins are not easily fused, expressed foreign proteins are frequently inactivated and the size of the foreign protein that can be inserted is limited to 60~70 amino acids (Georgiou, G. et al., *Nat. Biotechnol.*, 15:29, 1997; Stahl, S. et al., *Trends Biotechnol.*, 15:185, 1997).

As described above, the application area of cell surface display employing bacterial secretion system in Biotechnology is wide, and it is determined by the type of a foreign protein to be expressed on the surface of a cell. A bacterial vaccine containing epitopes originated from a pathogen, which is expressed on cell surface of a cell, can be applied to patients to induce stronger and more sustained immune response than conventional vaccines using attenuated pathogenic microbes or viruses (Nguyen, T. N. et al., *Gene*, 128:89, 1993). The screening of various peptides or antibodies, when a specific Fab or a single chain antibody as well as the above mentioned recombinant live vaccines is expressed on the surface of a cell, can be simply performed (Francisco, J. A. R. et al., *Proc. Natl. Acad. Sci. USA*, 1:10444, 1993). In addition, this technique is highly valuable for application such as antibody production by administrating bacteria expressing a specific antigen to animals (Charbit, A. et al., *Gene*, 70:181, 1988), whole cell absorbents applying to heavy metal elimination or waste water treatment using microbes expressing metal absorbing proteins on the cell surface (Sousa, C. et al., *J. Bacteriol.*, 180:2280, 1998), and whole-cell bioconversion utilizing enzymes used for biological conversion, which is stably expressed on the cell surface and used continuously without a decrease in catalytic activity (Richins, R. et al, *Nat. Biotechnol.*, 15:984, 1997).

Therefore, there is an urgent need in the art to develop a cell surface display technique which is useful in the various field of biotechnology, especially the development of a method in which a target protein is stably and effectively expressed in large amounts on the surface of bacteria, a new surface anchoring motif and a surface expression vector using the same.

Accordingly, the present inventors have made extensive efforts to develop a surface anchoring motif, which can effectively express a foreign protein on the surface of a microorganism, deliver the expressed protein to the surface of the cell, and stably overexpress a foreign protein with large size, and a vector using the same, and as a result found, when a recombinant expression vector was constructed using exosporium protein BclA derived from *Bacillus anthracis* as a cell surface anchoring motif, a foreign protein is effectively overexpressed on the surface of a transformant, thereby completing the present invention.

SUMMARY OF THE INVENTION

Therefore, it is an object of the present invention to provide a surface expression vector comprising bclA gene encoding *Bacillus anthracis* exosporium BclA as a cell surface anchoring motif or fragments thereof and a gene encoding a target protein, as well as a microorganism transformed with the surface expression vector.

Another object of the present invention is to provide a method for stably expressing a target protein on the cell surface in large amounts by culturing the transformed microorganism.

Still another object of the present invention is to provide a method for manufacturing a protein array, a method for producing an antibody, a bioconversion method, the method is characterized by using the target protein surface-expressed according to the above method, and a whole cell biosensor employing the interaction between biotin and a transformant expressing streptavidin on the surface thereof.

To achieve the above objects, in one aspect, the present invention provides a surface expression vector comprising bclA gene encoding *Bacillus anthracis* exosporium protein BclA as a cell surface anchoring motif or the fragments thereof and a gene encoding a promoter and a target protein, wherein the expression vector is constructed such that the target protein is expressed in a form fused with BclA or a fragment thereof on the surface of a cell when a gene encoding the target protein is expressed in a host cell.

The present invention, in another aspect, provides a transformed microorganism obtained by introducing the expression vector into a cell selected from the group consisting of Gram-positive bacteria, Gram-negative bacteria, *Actinomyces*, yeast and fungus.

The present invention, in still another aspect, provides a method for expressing a target protein on the surface of a cell, the method comprising the steps of: expressing the target protein on the cell surface by culturing the transformed microorganism; and recovering the cell having the target protein expressed on the surface thereof.

The present invention, in yet still another aspect, provides a bioconversion method, the method is characterized by using the cells prepared by the above method and expressing a target protein having an enzyme activity on the surface thereof.

The present invention, in yet still another aspect, provides a method for manufacturing a protein array, the method is characterized by attaching the cells prepared by the above method and expressing the target protein expressed on the surface thereof, on a substrate.

The present invention, in further another aspect, provides a method for producing an antibody in vertebrates, the method comprising the steps of: (a) inducing immune response by administrating the cells prepared by the above method and expressing an antigen on the surface thereof to a vertebrate except a human being, and (b) recovering the antibody produced by the immune response.

The present invention, in still further another aspect, provides a method for preparing of a chiral compound such as chiral esters, chiral organic acids or chiral alcohols by carrying out optical resolution of racemic ester compounds using lipase, the method is characterized by using the lipase expressed on the surface of the cells prepared by the above method.

The present invention, in yet further another aspect, provides a whole cell biosensor which comprises a recombinant microorganism transformed with an expression vector comprising a gene encoding streptavidin and a gene of exosporium protein BclA derived from *Bacillus anthracis* as a cell surface anchoring motif as an effective ingredient.

The present invention, in yet still another further aspect, provides a method for improving a target protein, the method comprising the steps of: (a) establishing a mutant library of a gene encoding a target protein; (b) constructing a gene recombinant containing the mutant library of the gene encoding the target protein and bclA gene; (c) transforming a host cell selected from the group consisting of Gram-positive bacteria, Gram-negative bacteria, *Actinomyces*, yeast and fungus, with the gene recombinant or a vector containing the gene recombinant; (d) expressing the mutant library of the gene on the cell surface by culturing the transformed host cell; and (e) screening cells on which the target protein having an improved properties was expressed.

The above and other features and embodiments of the present invention will be more fully apparent from the following detailed description and appended claims.

DETAILED DESCRIPTION OF THE INVENTION, AND PREFERRED EMBODIMENTS

In one aspect, the present invention relates to a surface expression vector comprising bclA gene encoding BclA, *Bacillus anthracis* exosporium protein as a cell surface anchoring motif or a fragment thereof, which is constructed such that the target protein can be expressed in a form fused with BclA or a fragment thereof on the surface of a cell when a gene encoding the target protein is expressed in a host cell, a microorganism transformed with the expression vector, and a method for expressing the target protein on the surface of a microorganism using the same. In the present invention, a fragment of bclA gene is preferably the N-terminal end of bclA gene of SEQ ID NO: 1, the N-terminal end and the C-terminal end of SEQ ID NO: 2 in which the middle part is deleted from bclA gene, and SEQ ID NO: 3.

In the present invention, the promoter used is preferably tac promoter or any other inducible promoter, and the target protein is preferably a protein prepared by deleting a part of amino acid sequences of the target protein or subjecting it to site-specific mutation in order to facilitate surface expression of the target protein.

In the present invention, the microorganism used for the transformation is preferably a microorganism mutated such that an intracellular or extracellular protease that degrades the expressed target protein cannot be produced, in order to facilitate surface expression of the target protein, more preferably *Escherichia coli*.

In the present invention, the target protein is preferably any one selected from the group consisting of hormones, hormone analogues, enzymes, enzyme inhibitors, signal transduction proteins or their fragments, antibodies or their fragments, single chain antibodies, binding proteins, binding domains, peptides, antigens, adherent proteins, structural proteins, regulatory proteins, toxin proteins, cytokines, transcription factors, blood coagulation factors, and plant defense-inducing protein. The target protein is preferably streptavidin and the enzyme is preferably lipase.

Figure 1:
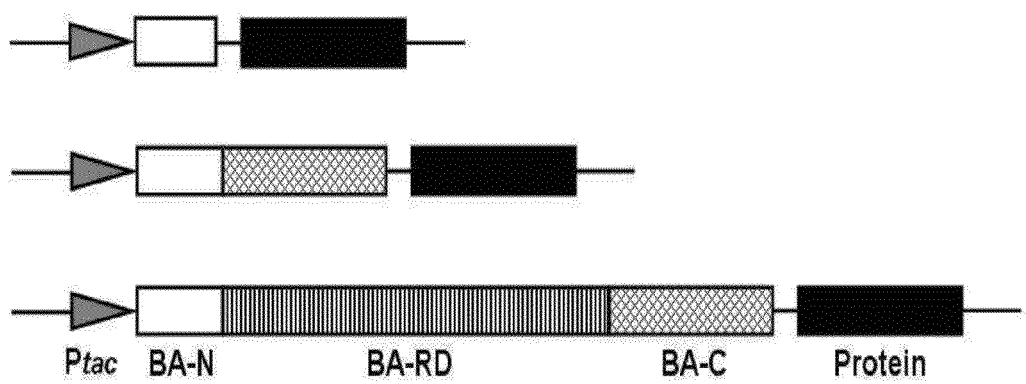
FIG. 1 shows structure characteristics resulting from cell surface display using *Bacillus anthracis* exosporium BclA.

The present inventors selected BclA, exosporium protein originated from *Bacillus anthracis* as a cell surface anchoring motif which has a highly effective secretion signal sequence and a targeting signal enabling a target protein to be stably attached on an outer cell membrane surface, and is capable of delivering a large size of target proteins and stably expressing a large amount of target proteins, for successful cell surface display. In addition, BclA according to the present invention is effective for cell surface display and stably expressing a large amount of target proteins, for successful cell surface display single unit spore of *Bacillus anthracis*. FIG. 1 is a schematic diagram showing characteristic structure resulting from cell surface display using BclA, *Bacillus anthracis* exosporium protein (Ptac; tac promoter, BA-N: the N-terminal end of BclA, BA-RD; GXX-amino-acid repeat region, BA-C; the C-terminal end of BclA, Protein; recombinant foreign protein). That is, as shown in FIG. 1, in the structure of BclA, *Bacillus anthracis* exosporium protein, the N-terminal end and the C-terminal end possess identical amino acid sequences regardless of the kind of *Bacillus anthracis* and three amino acids ($(GPT)_{1-8}GDTGTT$) appear repeatedly in the middle of the protein repeatedly (Sylvestre et al., *Mol. Microbiol.*, 45:169, 2002; Sylvestre et al., *J. Bacteriol.*, 185: 1555, 2003).

BclA is a collagen analogue protein which has the N-terminal end consisting of 40 amino acids and the C-terminal end consisting of 138 amino acids, and especially, is effective for cell surface display despite the absence of a specific secretion signal sequence at the N-terminal end (Sylvestre et al., *Mol Microbiol.*, 45:169, 2002; Sylvestre et al., *J. Bacteriol.*, 185:1555, 2003).

Accordingly, the present inventors predicted the structure of BclA, *Bacillus anthracis* exosporium protein to express a target protein on the cell surface using a surface anchoring motif containing the whole or part of exosporium protein.

In order to obtain bclA gene encoding an exosporium protein originated from *Bacillus anthracis*, bclA gene (NCBI accession No. AJ516945) of *Bacillus anthracis* RA3 (NCBI accession No. CAD56878) was synthesized from bclA gene distributed by Blue Heron Biotechnology Co. (Botell, Wash., USA) using de novo synthesis. EcoRI and XbaI sites of about 762 bp of DNA fragment, thus synthesized, was inserted into plasmid pTAC99A (Park and Lee, *Biotechnol. Tech.*, 12:815, 1998) together with a multi-cloning site using PCR (Polymerase Chain Reaction) in order to insert the target protein gene, thus preparing a recombinant plasmid, pTJ1-BA.

Figure 5:
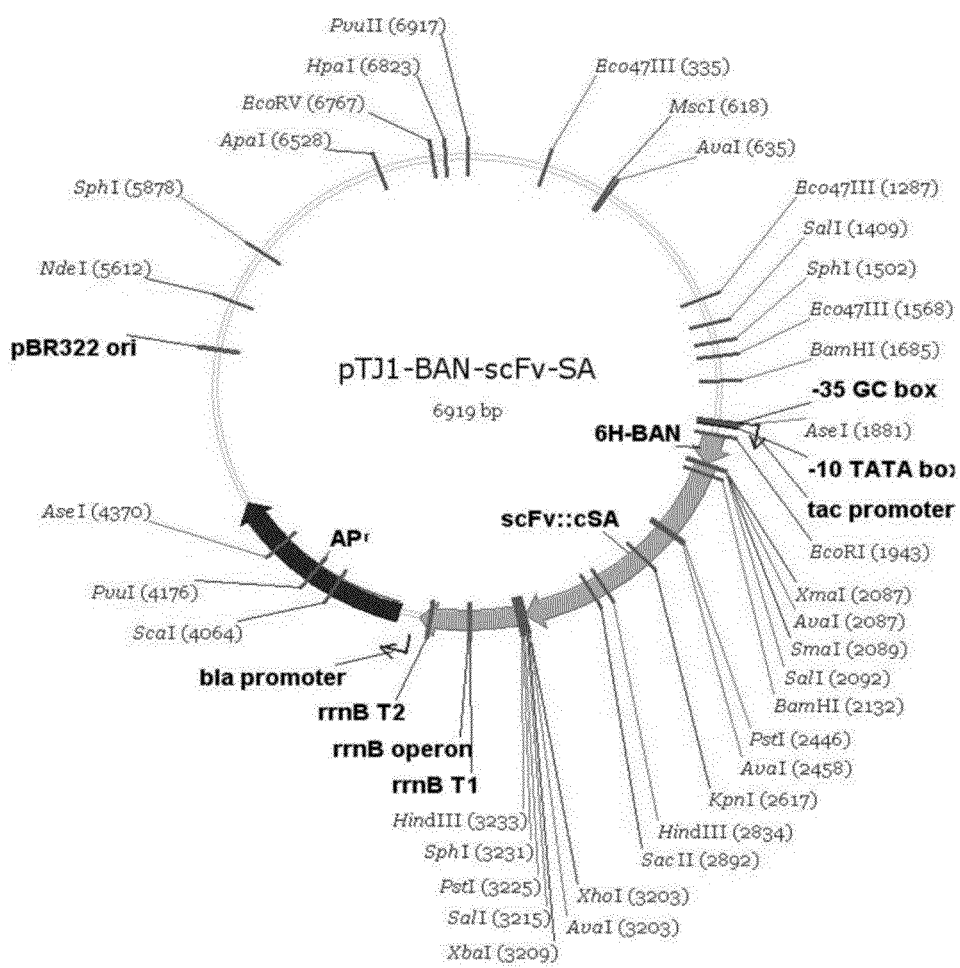
FIG. 5 to FIG. 7 are genetic maps of expression vectors, pTJ1-BAN-ScFv-SA, pTJ1-BANC-ScFv-SA and pTJ1-BAF-ScFv-SA, respectively.
Figure 6:
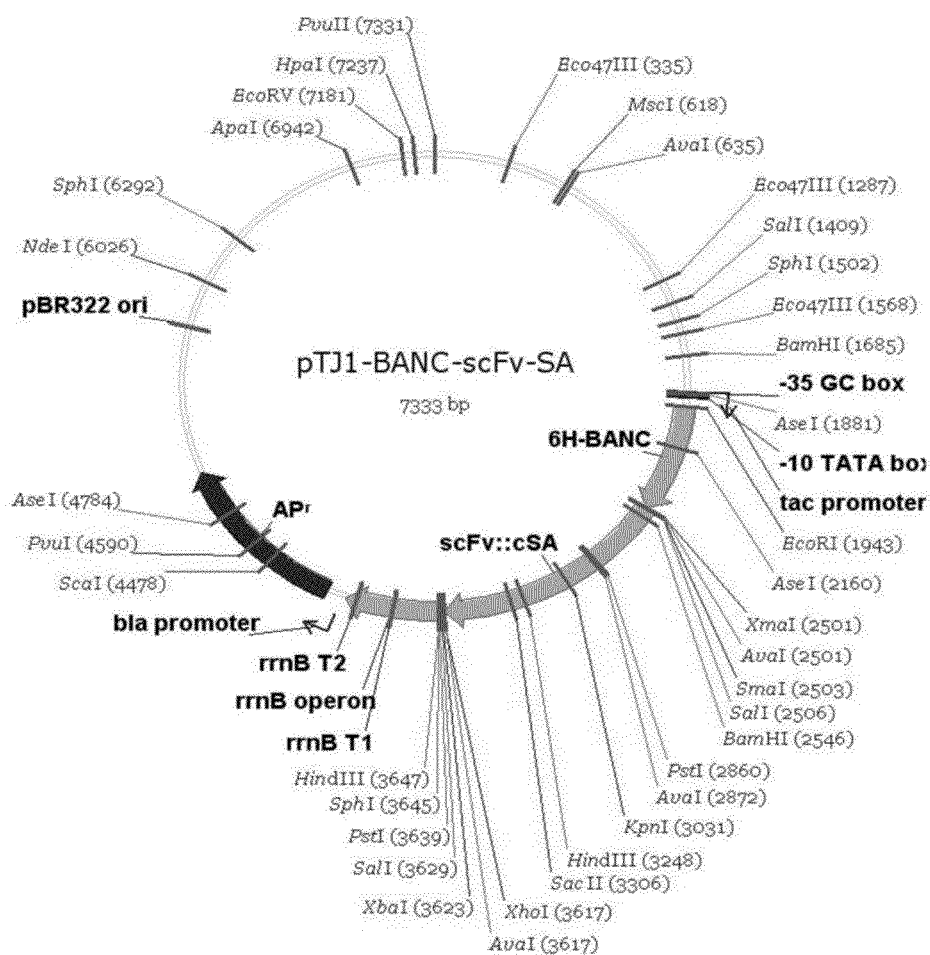

In the prepared recombinant plasmid, pTJ1-BA, *Bacillus anthracis* exosporium protein BclA is expressed by induction of tac promoter. For a model protein to be expressed on the surface of a cell, a gene in a form, where ScFv (a single chain antibody against a surface protein of Hepatitis B virus) is fused with cSA (core streptavidin), was inserted into cutting sites of restriction enzymes, XmaI and XhoI present in the C-terminal end of the exosporium protein, thus preparing a recombinant expression vector, pTJ1-BAF-ScFv-SA (FIG. 7). pTJ1-BAN-ScFV-SA and pTJ1-BANC-ScFV-SA were also prepared by the same method described above, in order to examine whether the N-terminal end, from which the repeated amino acid sequences, $(GPT)_{1-8}GDTGTT$ had been eliminated, or a fused form of the N-terminal end and the C-terminal end can be used on the surface of *E. coli* as a surface anchoring motif (FIG. 5 and FIG. 6).

In addition, pTJ1-BAN-Lip1 and pTJ1-BANC-Lip1 and pTJ1-BAF-Lip1 fused with lipase were prepared by the same method for preparing a fusion protein gene of a single chain antibody and streptavidin.

The prepared recombinant expression vectors, pTJ1-BAN-Lip1 and pTJ1-BANC-Lip1 or pTJ1-BAF-Lip1 was introduced into *E. coli*, XL1-Blue strain to culture thus obtained transformant, and an expression-inducing factor, for example, IPTG (isopropyl-β-thiogalactoside) was added to culture broth to induce the expression, and then a certain amount of the culture broth was taken to fractionate outer cell membrane proteins, followed by analyzing the fractionated proteins using SDS-PAGE (sodium dodecylsulfate polyacrylamide gel electrophoresis). As a result, it was confirmed that the fractionated proteins are successfully inserted into BclA, *Bacillus anthracis* exosporium protein to be expressed on the surface of the cell and also found that the amount of BclA, *Bacillus anthracis* exosporium protein fused with the desired proteins based on the whole outer cell membrane protein was 30%~45%, suggesting the rate is very high (FIG. 8).

Additionally, whether streptavidin (target protein) expressed successfully on the outer cell membrane of *E. coli* after being transformed with the prepared recombinant expression vectors, pTJ1-BAN-ScFV-SA, pTJ1-BANC-ScFV-SA or pTJ1-BAF-ScFv-SA has an activity was examined by protein-ligand interaction using biotin-coated fluorescent beads. As a result, it was found that, when a protein fused with BclA-ScFv-SA was expressed on the surface of the cell, biotin was successfully bound to streptavidin on the surface of the cell, resulting in high-level fluorescence (FIG. 9), The result suggests that all streptavidins (target proteins) expressed on the outer cell membrane were expressed on the outside surface of the cell. Especially, it was found that about 40 kDa of recombinant protein, which is relatively large size, was inserted to be successfully expressed on the cell surface, thus suggesting that the inventive BclA, *Bacillus anthracis* exosporium protein is a very effective surface anchoring motif.

In the present invention, when the target protein is expressed in a cell or on the outside of a cell, the target protein gene may be one or a gene repeated more than twice or the target protein gene repeated more than twice may be the same genes or different genes and also the target protein gene may be any combination of the above.

It is obvious to a person skilled in the art that the gene prepared by the method according to the present invention can be present independently in a plasmid or inserted in a chromosome of a host bacterium.

It is also obvious to a person skilled in the art that induction of target protein expression can be performed by a promoter capable of inducing the expression in a host cell, a promoter of a target protein gene or a proper other promoter capable of expressing in a host cell.

Meanwhile, the method according to the present invention may be applied to all proteins and used to modify and surface-express proteins such as hormones, hormone analogues, enzymes, enzyme inhibitors, antibodies, signal transduction proteins, single chain antibodies, antigens, peptides, polypeptides, binding proteins, binding domains, adherent proteins, structural proteins, regulatory proteins, toxin proteins, cytokines, various regulatory factors and their fragments.

There are various methods to prove that a target protein surface-expressed on the outer cell membrane of a microorganism by the inventive expression method described above exists on the cell surface. The methods are as follows: a method in which spores were fluorescently stained by binding a primary antibody to a target protein surface-expressed on the outer cell membrane of a microorganism and reacting it with a fluorescent-labeled secondary antibody to observe using fluorescence microscopy or analyze using flow cytometry. Herein, when the secondary antibody is labeled with gold, the target protein can be observed using electronic microscope.

A method of examining whether the enzyme activity is decreased or the signal of fluorescence microscope or flow cytometer is weakened due to the degradation of the surface-expressed proteins by protease placed from the outside.

And a method in the case where a target protein is an enzyme using a polymer material as a substrate, in which the existence of the target protein can be proved by the measured enzyme activity resulting from enzymes exposed on the cell surface since the substrate cannot pass through between outer surface structures of spores when measuring the enzyme activity.

In another aspect, the present invention relates to a bioconversion method, the method is characterized by using the cells prepared by the above method and expressing the target protein having an enzyme activity on the surface thereof.

In still another aspect, the present invention relates to a method for preparing a chiral compound such as chiral esters, chiral organic acids or chiral alcohols, by carrying out optical resolution of racemic ester compounds by using lipase, the method is characterized by using lipase expressed on the surface of the cells prepared by the above method.

In yet another aspect, the present invention relates to a method for manufacturing a protein array, the method comprising attaching the cells, prepared by the above method and expressing the target protein on the surface thereof, on a substrate.

Protein arrays provide the means to analyze expression or non-expression and the expression level of a target protein in specific cells by arraying various proteins, especially antibodies on a solid surface such as DNA chips or DNA arrays. For manufacturing a protein array, proteins to be arrayed are prepared, and then immobilized on a solid surface. Since analytical procedure using protein array includes a binding step to fixed proteins on a substrate and a washing step that removes unbound proteins under various conditions of high temperature, salt concentration and pH change, it therefore needs stable immobilization of proteins to overcome such stringent conditions.

However, the procedure of cloning thousands and ten thousands of protein genes into an expression vector, expressing and isolating the protein gene, followed by immobilizing on the surface of a solid requires many repeated operations. Therefore, the procedure needs to be conducted in a simple and rapid manner.

The method for manufacturing a protein array according to the present invention provides the means to carry out the above mentioned procedure in a simplest manner. According to the inventive method, a target protein expressed by the above method is isolated to immobilize on the surface of a solid. For the process of manufacturing a protein array according to the present invention, the conventional methods used in the art may be used (WO 00/61806; WO 00/54046; U.S. Pat. No. 5,807,754; EP 0818467; WO 97/42507; U.S. Pat. No. 5,114,674; WO 96/35953). The protein arrays prepared according to the present invention may be applied to detection kits, gene expression analysis, interaction analysis between proteins or between proteins and their ligands and between antibodies and antigens, analysis of metabolic pathway, searching novel enzymes or improved enzymes, combined biological synthesis and biosensors.

The solid substrate that can be used in the present invention may include glasses (for instance: glasses having functional groups exposed), Si, Ge, GaAs, GaP, SiO, $SiN_4$, modified silicone nitrocellulose, polyvinylidene fluoride, polystyrene, polytetrafluoroethylene, polycarbonate, nylon, fiber or the combination thereof. Said substrate may be fixed with linker molecules for protein immobilization and the rest area with no spotting is preferably blocked.

In yet still another aspect, the present invention relates to a method for preparing an antibody in vertebrates, the method comprising the steps of; (a) inducing an immune response by administering cells prepared by the above method and having an antigen expressed on the surface thereof to vertebrates except human beings; and (b) recovering the antibody produced by the immune response.

In yet still another aspect, the present invention relates to a whole cell biosensor which comprises a recombinant microorganism transformed with an expression vector containing a gene encoding exosporium protein BclA derived form *Bacillus anthracis* which is a cell surface anchoring motif and a gene encoding streptavidin as an effective ingredient. In the present invention, the transformant microorganism is preferably *E. coli*.

In yet still another aspect, the present invention relates to a method for improving a target protein, the method comprising the steps of; (a) establishing a mutant library of a gene encoding a target protein; (b) constructing a gene recombinant containing the mutant library of the gene encoding the target protein and bclA gene; (c) transforming a host cell selected from the group consisting of Gram-positive bacteria, Gram-negative bacteria, *Actinomyces*, yeast and fungus, with the gene recombinant or a vector containing the gene recombinant; (d) expressing the mutant library of the gene on the cell surface by culturing the transformed host cell; and (e) screening cells on which the target protein having an improved properties was expressed.

In the present invention, the screening step preferably uses an activity of the target protein, a protein recognizing a substance labeled to the target protein, a labeled ligand binding to the target protein, or an antibody binding specifically to the target protein.

In the method for improving a target protein according to the present invention, the construction of gene library may be carried out by mutating a wild type gene of a target protein, using DNA shuffling method (Stemmer, *Nature*, 370:389, 1994), StEP method (Zhao, H. et al., *Nat. Biotechnol.*, 16:258, 1998), RPR method (Shao, Z. et al., *Nucleic Acids Res.*, 26:681, 1998), Molecular breeding method (Ness, J. E. et al, *Nat. Biotechnol.* 17:893, 1999), ITCHY method (Lutz, S. et al., *Cur. Opi. Biotechnol.* 11:319, 2000), Error-prone PCR (Cadwell, R. C. et al., *PCR Methods Appl.*, 2:28, 1992), Point Mutation (Sambrook et al., *Molecular Cloning: A Laboratory Manual*, Cold Spring Harbor, N.Y., 1989), but it is not limited thereto.

In the method for improving a target protein according to the present invention, the screening step may be rapidly performed by measuring protein activity or FACS analysis (Georgiou, G., Adv. Protein Chem., 55:293, 2000). In the case where the protein activity is used, the screening can be carried out by measuring the growth of a host cell in which proteins are expressed or the reaction for color development catalyzed by proteins. Additionally, in the inventive method for improving a target protein using spore resistance, the screening step may be rapidly performed by using a protein activity or stability of protein structure.

When the method for improving proteins according to the present invention, which has the above mentioned characteristics, was used, enzymes catalyzing biologically non-occurring chemical reaction that cannot be easily obtained by conventional methods (for instance; Diels-Alder condensation reaction), enzymes having an activity of unnatural stereoselectivity or regioselectivity, enzymes capable of catalyzing a reaction in an organic solvent or an organic solvent-aqueous solution, enzymes catalyzing a reaction in an extreme condition such as a high pressure and a high temperature, etc, which cannot be easily obtained by conventional methods, can be rapidly obtained from wild-type enzymes.

Also, the inventive method for improving proteins may solve the problem of a decrease in the survival rate of bacteria upon reinoculating into a culture medium when eluted by a dramatic change in pH or by regulating base concentration for screening an antibody mutant with an increased binding ability.

Meanwhile, since it was confirmed that a microorganism transformed with a vector constructed, such that it expresses streptavidin as a foreign protein was interacted with biotin to effectively induce protein-ligand reaction, the present invention can be utilized for a biosensor by protein-ligand interaction, which contains a transformant, transformed with an expression vector constructed, such that it expresses on the cell surface in a form in which streptavidin is fused with BclA, as an effective ingredient.

Figure 10:
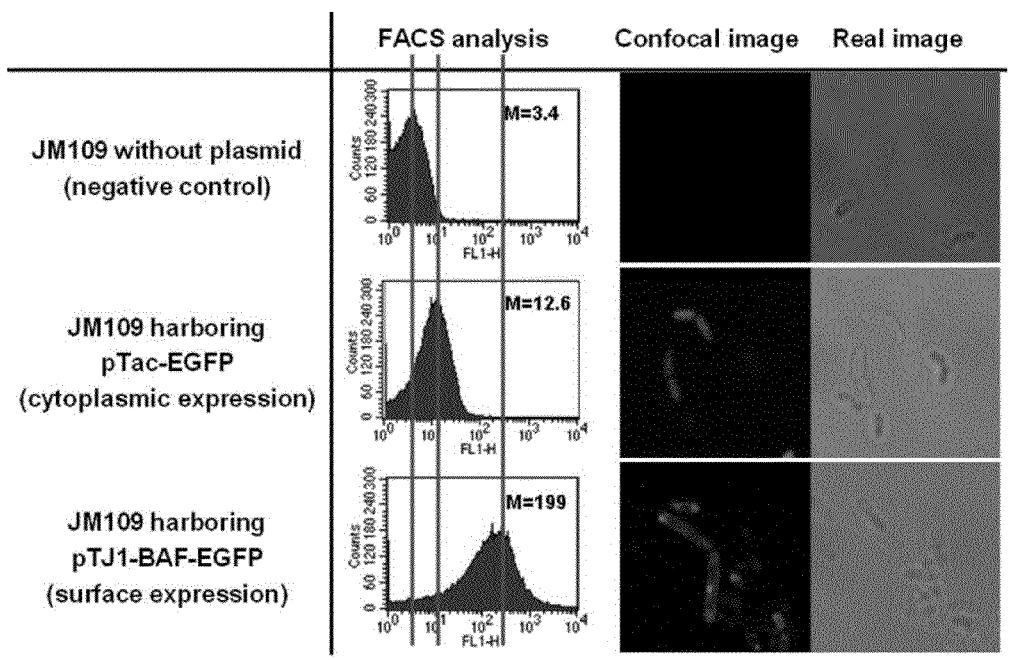
FIG. 10 shows the analysis results of recombinant *E. coli* transformed with an expression vector, pTJ1-BAF-EGFP using flow cytometry and confocal microscopy.

Furthermore, the expression of fluorescent substance on a recombinant *E. coli* was observed using confocal laser microscopy after *Bacillus anthracis* exosporium, BclA had been fused with a green fluorescent protein (FIG. 10). As a result, it was found that the green fluorescent protein was successfully expressed on the surface of *E. coli* JM109 transformant with a recombinant expression vector, expressing the green fluorescent protein fused with BclA, compared with the green fluorescent protein expressed in cells. Therefore, the recombinant *E. coli* according to the present invention can be used as a biosensor using protein-ligand interaction and a fluorescent sensor using proteins expressed on the cell surface.

EXAMPLES

The present invention will hereinafter be described in further detail by examples. It will however be obvious to a person skilled in the art that these examples are given for illustrative purpose only, and the scope of the present invention is not limited to these examples.

Especially, as a foreign gene, not only streptavidin gene described in examples below but also various target proteins or peptide genes are introduced into the expression vectors, pTJ1-BAN, pTJ1-BANC, pTJ1-BAF according to the present invention to be used for the expression thereof. Therefore, recombinant expression vectors, pTJ1-BAN, pTJ1-BANC, pTJ1-BAF inserted with various kinds of genes should be also considered to be in the scope of the present invention Example 1

Construction of Recombinant Expression Vector pTJ1-BA

In order to obtain *Bacillus anthracis* exosporium BclA gene, BclA gene of *Bacillus anthracis* RA3 (NCBI accession No. CAD56878) was synthesized to perform PCR using the synthesized gene as a template. The PCR was performed under the following conditions; 30 cycles of first denaturation at 94° C. for 7 min, second denaturation at 94° C. for 1 min, annealing at 55° C. for 1 min, extension at 72° C. for 1 min, and the last extension at 72° C. for 7 min using primers of SEQ ID NO: 4 and SEQ ID NO: 5.

```
SEQ ID NO: 4:
5'-GGAATTCATGTCAAATAATAATTATTC-3'

SEQ ID NO: 5:
5'-CGTCTAGACTCGAGGCTAGCCCCGGGAGCAACTTTTTCAATAA-3'
```

770 bp of DNA fragment obtained by the PCR was isolated using agarose gel electrophoresis, and digested with two restriction enzymes, EcoRI and XbaI. At the same time, plasmid pTac99A (Park and Lee, *Biotechnol. Techn.*, 12:815, 1998) containing inducible and strong tac promoter was digested with two restriction enzymes EcoRI and XbaI and mixed with the resulting DNA fragment, and then linked with T4 DNA ligase, followed by transforming into *E. coli* XL1-Blue using electroporation. The transformed strain was screened on LB agar medium containing an antibiotic, ampicillin (100 μg/mL) and thus obtaining recombinant plasmid pTJ1-BA.

In the recombinant plasmid pTJ1-BA prepared as described above, exosporium protein BclA gene to be used as a surface anchoring motif can be expressed by strong, inducible tac promoter. The multicloning site of the recombinant plasmid pTJ1-BA contains the cutting sites of restriction enzymes XmaI and XhoI, and a target protein gene to be expressed on the cell surface is inserted into the cutting sites.

Example 2

Construction of Recombinant Vectors pTJ1-BAN, pTJ1-BANC and pTJ1-BAF

*Bacillus anthracis* exosporium BclA used as a cell surface anchoring motif has a repeated amino acid sequence, $(GPT)_{1-8}GDTGTT$ between the N-terminal end and the C-terminal end (Sylvestre et al., *Mol Microbiol.*, 45:169, 2002).

2-1: Construction of Recombinant Expression Vector pTJ1-BAN

In order to examine whether only the N-terminal end can be used as a cell surface anchoring motif, each cell surface anchoring motif was designed such that they can be fused with a target protein.

For the construction of a plasmid to use the N-terminal end of BclA gene as a cell surface anchoring motif, PCR was performed under the following conditions; 30 cycles of first denaturation at 94° C. for 5 min, second denaturation at 94° C. for 30 sec, annealing at 56° C. for 30 sec, extension at 72° C. for 30 sec, and the last extension at 72° C. for 7 min using primers of SEQ ID NO: 4 of Example 1 and SEQ ID NO: 6.

```
SEQ ID NO: 6:
5'-AGTCTAGACTCGAGGCTAGCCCCGGGGGTAGGAAGGGTAAATGG-3'
```

90 bp of DNA fragment obtained by the PCR was isolated using agarose gel electrophoresis, and digested with two restriction enzymes, EcoRI and XbaI. At the same time, plasmid pTac99A (Park and Lee, *Biotechnol. Techn.*, 12:815, 1998) containing inducible and strong tac promoter was digested with two restriction enzymes, EcoRI and XbaI and mixed with the resulting DNA fragment, and then linked with T4 DNA ligase, followed by transforming into *E. coli* XL1-Blue using electroporation. The transformed strain was screened on LB agar medium containing antibiotic, ampicillin (100 μg/mL), thus obtaining the recombinant pTJ1-BAN.

Figure 2:
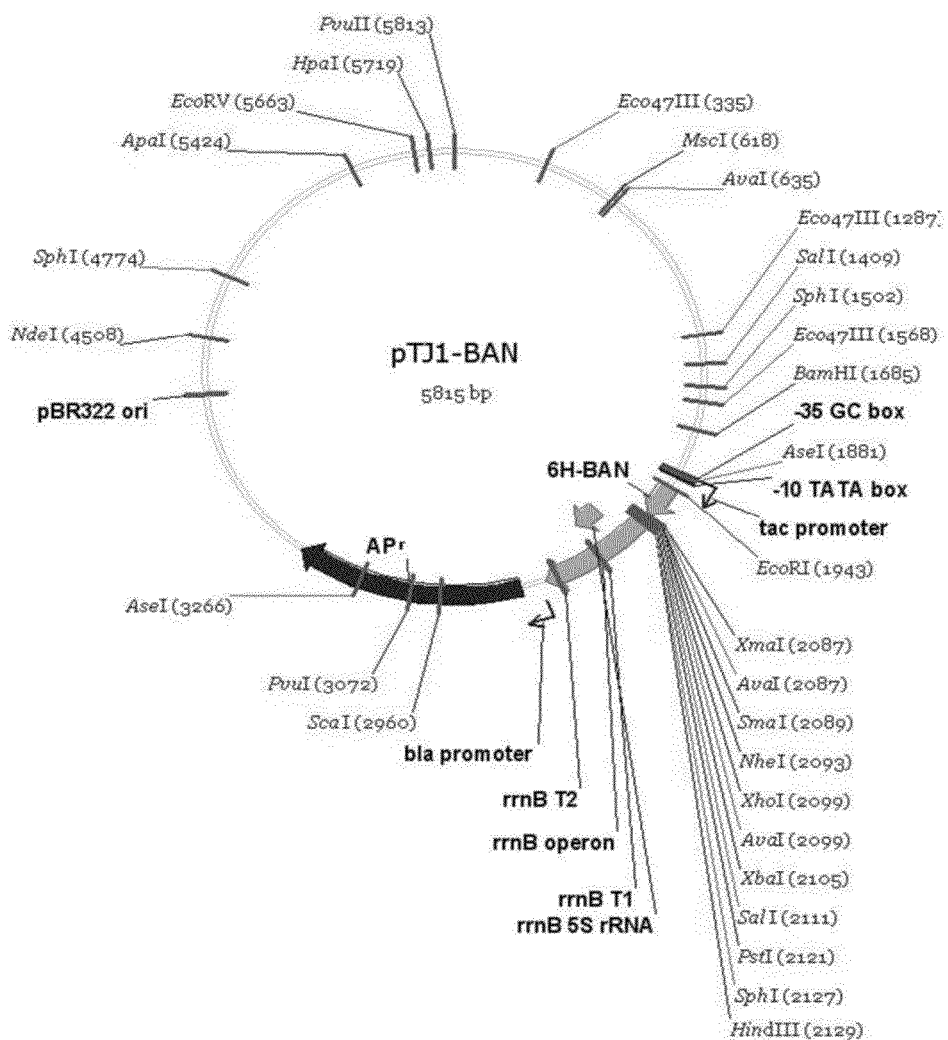
FIG. 2 to FIG. 4 are genetic maps of expression vectors, pTJ1-BAN, pTJ1-BANC and pTJ1-BAF, respectively.

In the recombinant plasmid pTJ1-BAN prepared as described above, the N-terminal end of exosporium protein BclA gene to be used as a surface anchoring motif can be expressed by strong, inducible tac promoter. The multicloning site of the recombinant plasmid pTJ1-BAN contains cutting sites of restriction enzymes, XmaI and XhoI, and a target protein gene to be expressed on the cell surface is inserted into the cutting sites. The genetic map of the recombinant expression vector constructed as described above is shown in FIG. 2.

2-2: Construction of Recombinant Expression Vector pTJ1-BANC

In order to examine whether only the N-terminal end and the C-terminal end of BclA, from which a repeated amino acid sequence, $(GPT)_{1-8}GDTGTT$ is deleted, can be used as a surface anchoring motif, each surface anchoring motif was designed such that they can be fused with a target protein.

In order to examine whether a fused form of the N-terminal end and the C-terminal end of BclA gene can be used as a surface anchoring motif, each surface anchoring motif was designed such that they can be fused with a target protein.

For the construction of a plasmid to use the N-terminal end and the C-terminal end of BclA gene as a surface anchoring motif, PCR was performed. A gene at the N-terminal end of BclA was amplified using primers of SEQ ID NO: 4 in Example 1 and SEQ ID NO: 7, and a gene at the C-terminal end of BclA was amplified using SEQ ID NO: 5 in Example 1 and SEQ ID NO: 8.

```
SEQ ID NO: 7:
5'-CCTAGTCCGGATGGCCCGGTAGGAAGGGTAAATGGT-3'

SEQ ID NO: 8:
5'-ACCATTTACCCTTCCTACCGGGCCATCCGGACTAGG-3'
```

Since each DNA of the N-terminal end and the C-terminal end of thus amplified BclA has an overlapped sequence, they are amplified again by PCR using primers of SEQ ID NO: 4 and SEQ ID NO: 5. PCR was performed under the following conditions; 30 cycles of first denaturation at 94° C. for 5 min, second denaturation at 94° C. for 45 sec, annealing at 56° C. for 45 sec, extension at 72° C. for 40 sec, and the last extension at 72° C. for 7 min.

560 bp of DNA fragment obtained by the PCR was isolated using agarose gel electrophoresis, and digested with two restriction enzymes, EcoRI and XbaI. At the same time, plasmid pTac99A (Park and Lee, *Biotechnol. Techn.*, 12:815, 1998) containing inducible and strong tac promoter was digested with two restriction enzymes, EcoRI and XbaI and mixed with the resulting DNA fragment, and then linked with T4 DNA ligase, followed by transforming into *E. coli* XL1-Blue using electroporation. The transformed strain was screened on LB agar medium containing antibiotic, ampicillin (100 μg/mL), thus obtaining the recombinant pTJ1-BANC.

Figure 3:
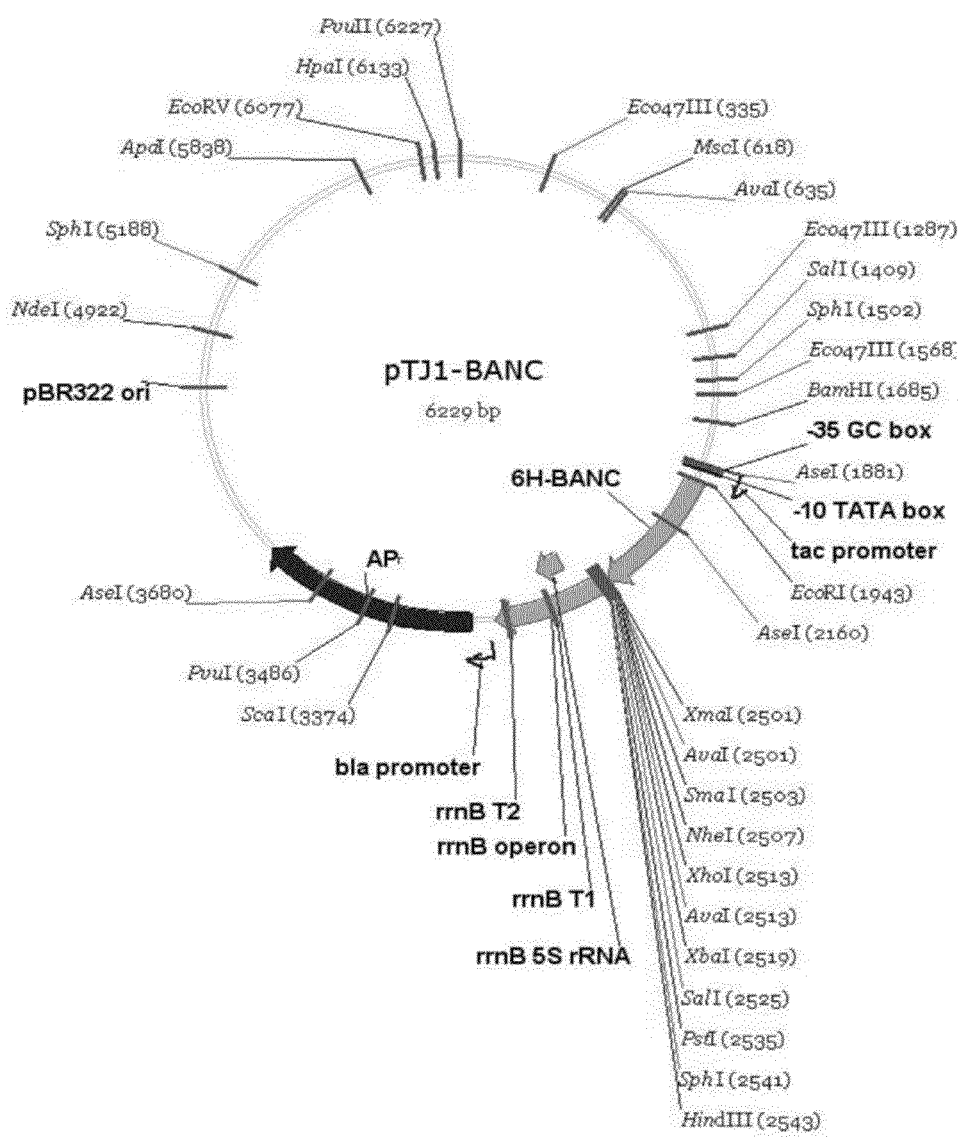

In the recombinant plasmid pTJ1-BANC prepared as described above, a fused gene of the N-terminal end and the C-terminal end of exosporium protein BclA gene to be used as a surface anchoring motif can be expressed by strong, inducible tac promoter. The multicloning site of the recombinant plasmid pTJ1-BAN contains cutting sites of restriction enzymes, XmaI and XhoI, and a target protein gene to be expressed on the cell surface is inserted into the cutting sites. The genetic map of the recombinant expression vector constructed as described above is shown in FIG. 3.

2-3: Construction of Recombinant Expression Vector pTJ1-BAF

In order to examine whether the N-terminal end, a repeated amino acid sequence (GPT)$_{1-8}$GDTGTT, and the C-terminal end of BclA can be used as a surface anchoring motif, each surface anchoring motif was designed such that they can be fused with a target protein.

In order to examine whether BclA gene can be used as a surface anchoring motif, each surface anchoring motif was designed such that they can be fused with a target protein.

For the construction of a plasmid to use BclA gene as a cell surface anchoring motif, BclA gene was amplified by PCR under the following conditions; 30 cycles of first denaturation at 94° C. for 5 min, second denaturation at 94° C. for 45 sec, annealing at 56° C. for 45 sec, extension at 72° C. for 1 min, and the last extension at 72° C. for 7 min using primers of SEQ ID NO: 4 and SEQ ID NO: 5 of Example 1.

780 bp of DNA fragment obtained by the PCR was isolated using agarose gel electrophoresis, and digested with two restriction enzymes, EcoRI and XbaI. At the same time, plasmid pTac99A (Park and Lee, *Biotechnol. Techn.*, 12:815, 1998) containing inducible and strong tac promoter was digested with two restriction enzymes, EcoRI and XbaI and mixed with the resulting DNA fragment, and then linked with T4 DNA ligase, followed by transforming into *E. coli* XL1-Blue using electroporation. The transformed *E. coli* was screened on LB agar medium containing antibiotic, ampicillin (100 µg/mL), thus obtaining the recombinant pTJ1-BAF.

Figure 4:
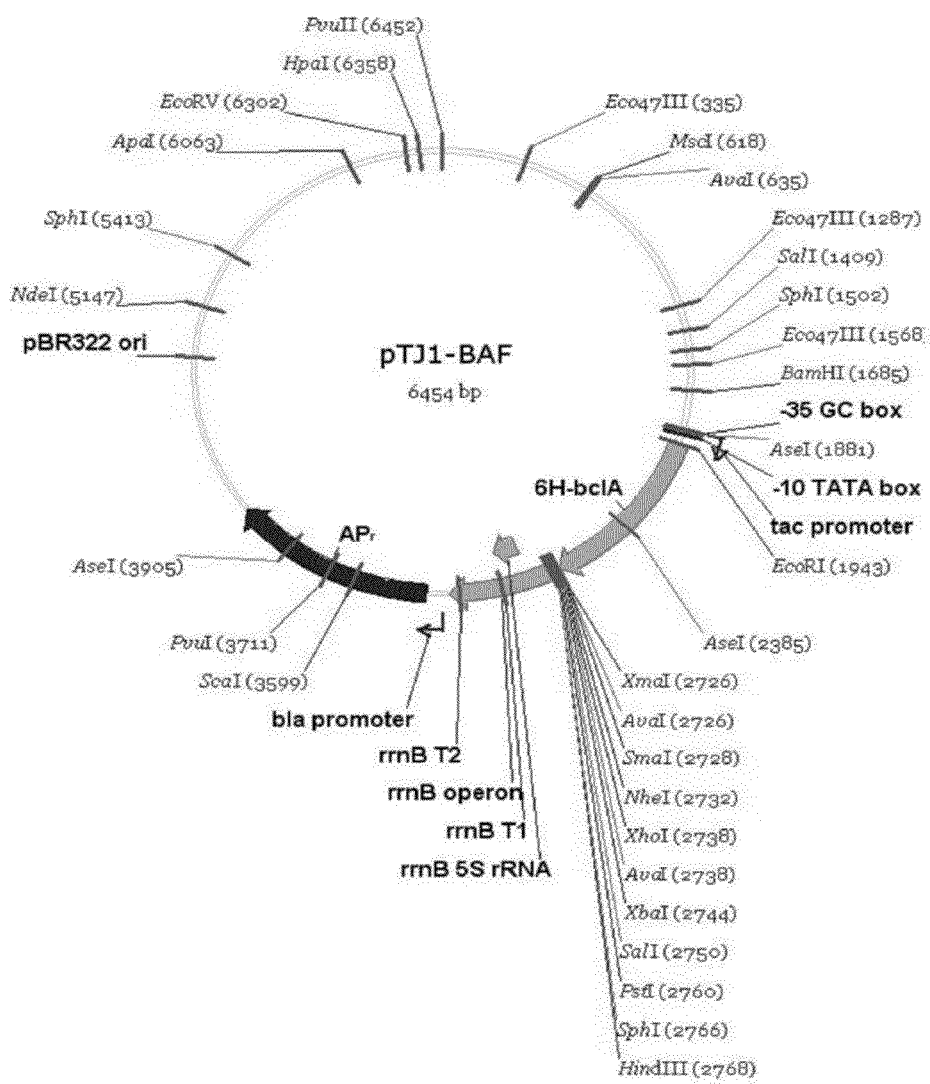

In the recombinant plasmid pTJ1-BAF prepared as described above, exosporium protein BclA gene to be used as a surface anchoring motif can be expressed by strong, inducible tac promoter. The multicloning site of the recombinant plasmid pTJ1-BAF contains the cutting sites of restriction enzymes, XmaI and XhoI, and a target protein gene to be expressed on the cell surface is inserted into cutting sites. The genetic map of the recombinant expression vector constructed as described above is shown in FIG. 4.

Example 3

Construction of Recombinant Expression Vectors, pTJ1-BAN-ScFv-SA, pTJ1-BANC-ScFv-SA and pTJ1-BAF-ScFv-SA, and pTJ1-BAN-Lip1, pTJ1-BANC-Lip1 and pTJ1-BAF-Lip1

As a model protein expressed on the cell surface, recombinant expression vectors, pTJ1-BAN-ScFv-SA, pTJ1-BANC-ScFv-SA and pTJ1-BAF-ScFv-SA, and pTJ1-BAN-Lip1, pTJ1-BANC-Lip1 and pTJ1-BAF-Lip1 were constructed using a fusion protein of a single chain antibody and streptavidin and lipase.

3-1 Construction of Recombinant Expression Vectors, pTJ1-BAN-ScFv-SA, pTJ1-BANC-ScFv-SA and pTJ1-BAF-ScFv-SA In order to obtain a fusion protein gene of a single chain antibody and streptavidin, PCR was performed under the following conditions; 30 cycles of first denaturation at 94° C. for 5 min, second denaturation at 94° C. for 30 sec, annealing at 56° C. for 30 sec, extension at 72° C. for 1 min 10 sec, and the last extension at 72° C. for 7 min using primers of SEQ ID NO: 9 and SEQ ID NO: 10.

```
SEQ ID NO: 9:
5'-TTTACCCGGGTCGACTGAGGAGTCTGGA-3'

SEQ ID NO: 10:
5'-CTAGCTAGCCTCGAGTTACGGCTTCACCTTGGT-3'
```

Figure 7:
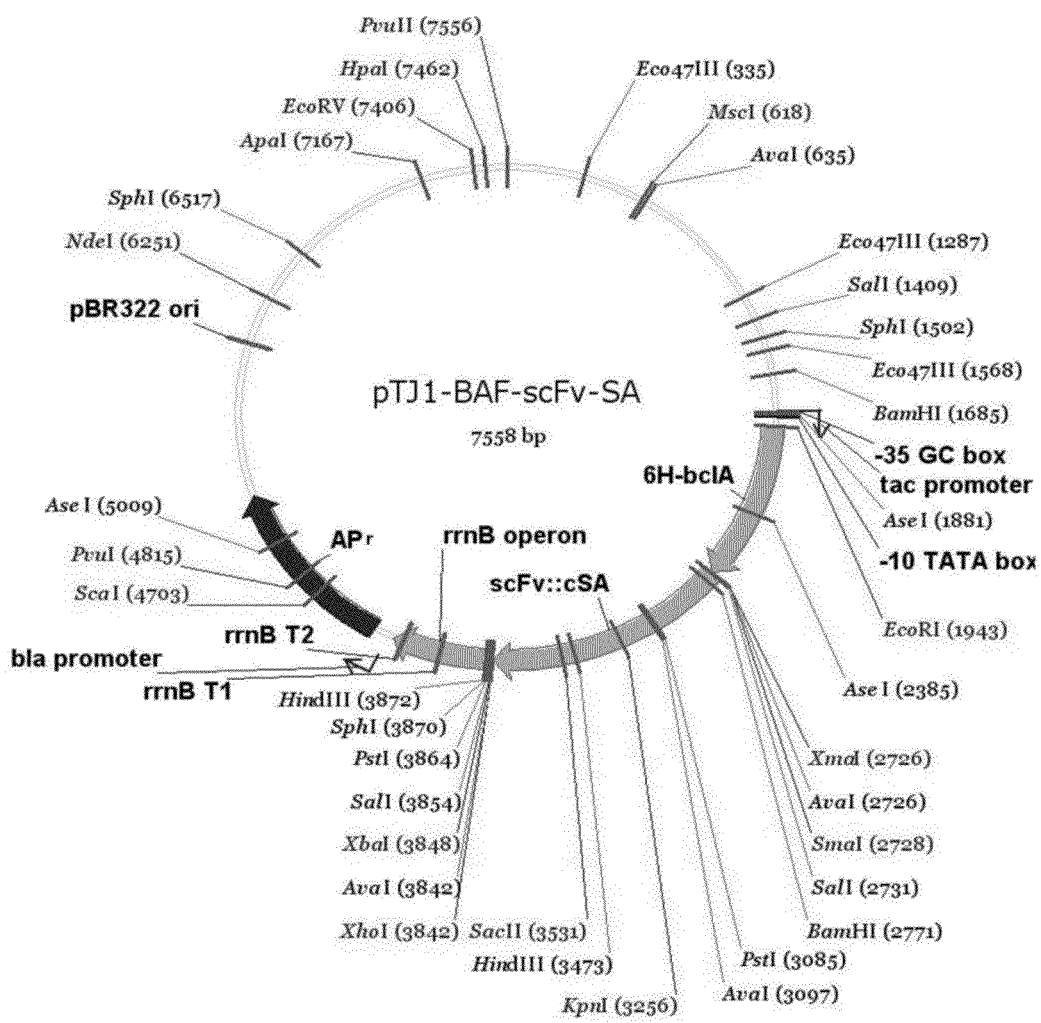

1120 bp of DNA fragment obtained by the PCR was isolated using agarose gel electrophoresis. Because the fusion gene of single chain antibody and streptavidin has XmaI site at the 5'-end, and XhoI and NheI sites at the 3'-end, the amplified product was digested with XmaI and XhoI. The digested DNA fragment was inserted into the same site as pTJ1-BAN, pTJ1-BANC and pTJ1-BAF prepared in Example 2 using T4 DNA ligase, followed by transforming into *E. coli* JM109 by electroporation. The transformed strain was screened on LB agar medium containing antibiotic, ampicillin (100 µg/mL), thus obtaining recombinant vectors, pTJ1-BAN-ScFv-SA, pTJ1-BANC-ScFv-SA and pTJ1-BAF-ScFv-SA (FIG. 5 to FIG. 7).

3-2: Construction of Recombinant Expression Vectors pTJ1-BAN-Lip1, pTJ1-BANC-Lip1 and pTJ1-BAF-Lip1

In the case of using lipase, recombinant expression vectors, pTJ1-BAN-Lip1, pTJ1-BANC-Lip1 and pTJ1-BAF-Lip1 were constructed using the same method as the method for preparing the fusion gene of a single chain antibody and streptavidin. PCR was performed using primers of SEQ ID NO: 11 and SEQ ID NO: 12.

```
SEQ ID NO: 11:
5'-ATAGCTAGCGCGGCTTCGCGAGCCAAT-3'

SEQ ID NO: 12:
5'-TAACAAGCTTTTAAGGCCGCAAACTCGC-3'
```

1170 bp of DNA fragment obtained by the PCR was isolated using agarose gel electrophoresis, and digested with restriction enzymes, NheI and HindIII. The digested fragment was inserted into the same site as the site of pTJ1-BAN, pTJ1-BANC and pTJ1-BAF prepared in Example 2 using T4 DNA ligase, followed by transforming into *E. coli* XL1-Blue by electroporation. The transformed strain was screened on LB agar medium containing antibiotic, ampicillin (100 µg/mL), thus obtaining recombinant vectors, pTJ1-BAN-Lip1, pTJ1-BANC-Lip1 and pTJ1-BAF-Lip1 expressing lipase.

Example 4

Expression of BclA Fusion Protein

The expression of *Bacillus anthracis* exosporium BclA fused with a model protein, lipase derived from *Bacillus* was examined in *E. coli* XL1-Blue (SupE44 hsdR17 recA1 endA1 gyrA96 thi relA1 lac F' (proBA+ lacIq lacZM15 Tn10 (tetr))) transformed with recombinant expression vectors, pTJ1-BAN-Lip1, pTJ1-BANC-Lip1 and pTJ1-BAF-Lip1 constructed by the method described in Example 3, respectively, using SDS-PAGE method.

Specifically, in order to examine the expression of BclA-Lip1 fusion protein, the recombinant *E. coli* was inoculated in a 250 ml of Erlenmeyer flask containing 50 ml of LB liquid medium and cultured at 37° C. Since the recombinant expression vectors have tac promoter, the expression was induced by adding IPTG (isopropyl-β-thiogalactoside). The induction of gene expression was carried out by adding 1 mM IPTG when the optical density (OD) at 600 nm reaches 0.6.

4 hours after the induction, each 3 ml of cultured broth was taken, and outer cell membrane proteins were fractionated. Specifically, 3 ml of culture broth was centrifuged at 4° C., 10,000 rpm, for 2 min to remove supernatant, and washed with 1 ml of Na$_2$HPO$_4$ (pH 7.2) buffer solution once, and centrifuged again at 4° C. 13,000 rpm, for 2 min, followed by suspending in 0.2 ml of Na$_2$HPO$_4$ (pH 7.2) buffer solution. The suspended solution was subjected to sonication to disrupt all the cells in the suspension, and centrifuged at room temperature, 10,000 rpm, for 2 min, thus obtaining supernatant from which debris is removed. For the protein fractionation of the cell membrane, the supernatant was centrifuged at room temperature, 13,000 rpm, for 30 min, and suspended in a buffer solution containing 0.5 ml of 0.5% (w/v) sarcosyl and 10 mM $Na_2HPO_4$ (pH 7.2). The cell membrane protein solution was allowed to react at 37° C. for 30 min, and centrifuged at 4° C., 13,000 rpm, for 30 min to fractionate insoluble phase. After the insoluble fraction was washed with 10 mM $Na_2HPO_4$ (pH 7.2) buffer solution and suspended in 50 µL of PBS (0.274 M NaCl, 0.041 M $Na_2HPO_4$, 0.047 M $KH_2PO_4$, 0.005 M KCl, pH 7.4), thus obtaining fractionated outer cell membrane protein sample solution (Puenete, J. L. et al., *Gene*, 156:1, 1995).

40 µL of proteins obtained by the above mentioned method was mixed with 10 µL of SDS-PAGE sample buffer solution (60 mM Tris-HCl; 25% glycerol; 2% SDS; 14.4 mM 2-mercaptoethanol; 0.1% bromophenolblue), and the mixture was allowed to react by heating in a boiling water bath for 10 min to perform SDS-PAGE gel electrophoresis on a 12% separating gel. After electrophoresis, the gel was stained by soaking in a dye solution (0.25 g/L Coomassie brilliant blue R; 40% Methanol; 10% Acetic acid) for more than 2 hours and destained by soaking twice in a destaining solution (40% methanol; 7% acetic acid) for more than 2 hours everytime (FIG. 8).

Figure 8:
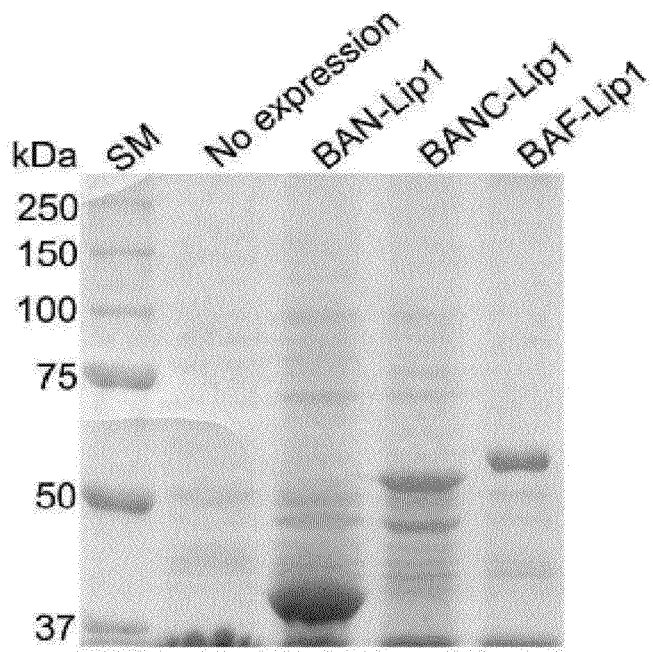
FIG. 8 is an electrophoresis photograph showing the analysis result of cell outer membrane proteins fractionated from a recombinant *E. coli* transformed with expression vectors, pTJ1-BAN-Lip1, pTJ1-BANC-Lip1 and pTJ1-BAF-Lip1 on SDS-PAGE gel.
Figure 9:
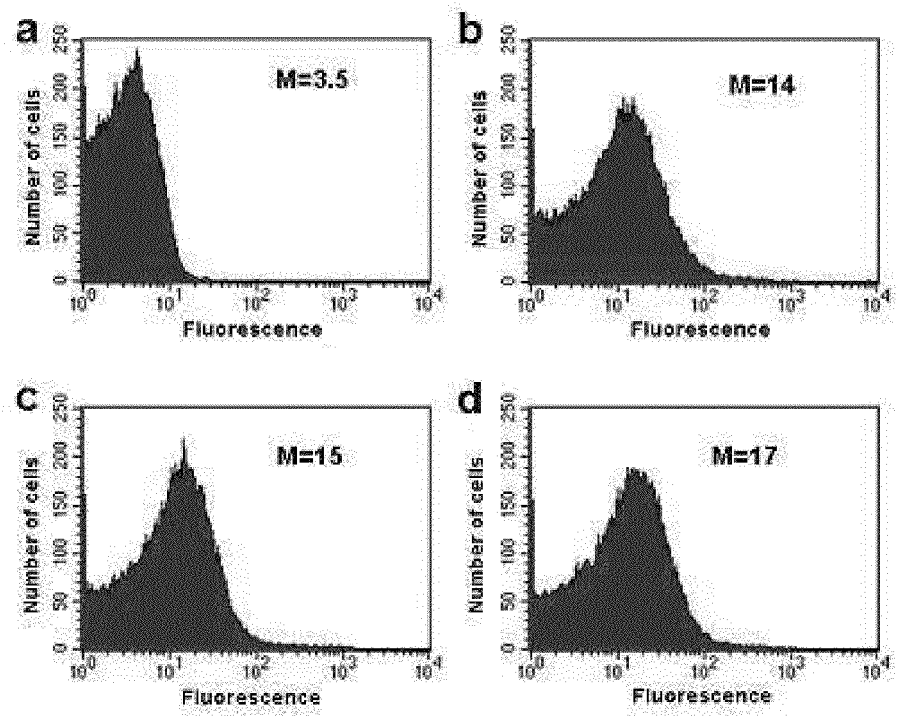
FIG. 9 shows the analysis results of recombinant *E. coli* transformed with expression vectors, pTJ1-BAN-ScFv-SA, pTJ1-BANC-ScFv-SA and pTJ1-BAF-ScFv-SA using flow cytometry.

Lane SM (size marker) in FIG. 8 is a size control group representing protein molecular weight standard (250 kDa, 150 kDa, 100 kDa, 75 kDa, 50 kDa and 37 kDa); first lane is the fraction of outer cell membrane protein from wild type XL1-Blue (no expression of BclA-Lip1 fusion protein), second to fourth lanes are outer cell membrane protein fractionation of *E. coli* XL1-Blue transformed with expression vectors, pTJ1-BAN-Lip1, pTJ1-BANC-Lip1 and pTJ1-BAF-Lip1, 4 hours after IPTG induction.

After electrophoresis as shown in FIG. 8, it was confirmed that each fusion protein, 45 kDa of BAN-Lip1, 61 kD of BANC-Lip1 and 66 kDa of BAF-.Lip1 was expressed on the outer cell membrane of *E. coli*, which suggests that 43 kDa of lipase (Lip1) was successfully inserted into the exosporium protein BclA and expressed on the outer cell membrane of *E. coli*.

In addition, said SDS-PAGE results was used to quantify proteins using densitometer to determine the ratio of outer cell membrane proteins, into which Lip1 proteins are inserted, to outer cell membrane proteins. Herein, the ratio was 30%~45%, suggesting that the expression rate is very high.

Example 5

Cell Surface Display of Recombinant *E. coli* Containing Recombinant Expression Vectors, pTJ1-BAN-ScFv-SA, pTJ1-BANC-ScFv-SA and pTJ1-BAF-ScFv-SA As shown in FIG. 9, FACS analysis was performed to examine whether a target protein fused with BclA is expressed on the cell surface, using recombinant *E. coli* having recombinant expression vectors, pTJ1-BAN-ScFv-SA, pTJ1-BANC-ScFv-SA and pTJ1-BAF-ScFv-SA constructed in Example 3.

Using the same condition as described in Example 4, cells transformed with recombinant expression vectors, pTJ1-BAN-ScFv-SA, pTJ1-BANC-ScFv-SA and pTJ1-BAF-ScFv-SA were cultured. 4 hours after the induction of the expression, 1 ml of culture broth was centrifuged at 4° C., 6,000 rpm for 5 min, to remove supernatant, and washed with PBS buffer solution twice, and then suspended in PBS buffer solution. Cell-bead mixture solution was treated with a solution of biotin bound to a fluorescent substance, and allowed to react at 37° C. for 1 hr. The resulting reaction solution was centrifuged at room temperature, 10,000 rpm for 10 min to remove supernatant and washed three times with PBS buffer solution, and then resuspended in PBS buffer solution, followed by analyzing with FACS (Fluorescent-Activated Cell Sorter, Beckton Dickinson, Fullerton, Calif., USA) (FIG. 9). The sample was excited at 543 nm by Helium/Neon Laser and the image was filtered through 580 nm filter.

In FIG. 9, a is an analytical result of wild type *E. coli*, XL1-Blue control, b is a result of *E. coli* XL1-Blue transformed with pTJ1-BAN-ScFv-SA, c is the result of *E. coli* XL1-Blue transformed with pTJ1-BANC-ScFv-SA, and d is the result of *E. coli* XL1-Blue transformed with pTJ1-BAF-ScFv-SA.

As shown in FIG. 9, it was confirmed that all three types of BclA fusion proteins were expressed on the outer cell membrane of *E. coli*, thus increasing fluorescent intensity of FACS, which means that the target proteins fused with BclA, *Bacillus anthracis* exosporium protein were successfully expressed on the outer cell membrane of *E. coli.*

From the result of the experiments, it was confirmed that a single chain antibody-streptavidin fused to BclA was successfully expressed on the outer cell membrane of *E. coli.*

Example 6

Realtime Analysis of Recombinant *E. coli* Containing Recombinant Expression Vector pTJ1-BA-EGFP After a fluorescent protein, EGFP (Enhanced Green Fluorescent Protein) was bound to the recombinant expression vector pTJ1-BA prepared in Example 1, Laser scanning confocal microscopy (Carl Zeiss LSM 410, Oberkochen, Germany) was used to examine (FIG. 10) whether green fluorescent proteins expressed in recombinant *E. coli* JM109 (F-ompT shdSB(rB-mB-) gal dcm(DE3)) is expressed on the cell surface.

Cells were cultured using the same condition as described in Example 4. 4 hours after induction of the expression, cells were collected by centrifugation, washed with an LB medium, transferred to IPTG-free LB medium, and cultured again for 4 hours in order to send the green fluorescent protein, remaining in cells while being expressed, to the cell surface. As a result, as shown in FIG. 10, the photograph of confocal laser scanning microscopy and FACS revealed that the location of GFP (without fusing with BclA) expressed in cells was different from that of GFP fused with BclA and expressed on the outer cell surface.

INDUSTRIAL APPLICABILITY

As described and proved above, the present invention provides an expression vector capable of effectively expressing a target protein or a peptide on the cell surface using BclA, *Bacillus anthracis* exosporium protein as a cell surface anchoring motif, and a microorganism transformed with the expression vector and a method for stably expressing the target protein in large amounts on the cell surface by culturing the transformed microorganism.

Also, when a foreign protein is expressed on the cell surface using the newly developed surface expression vector, it can be effectively used for the applications to recombinant live vaccines showing stronger and more sustained immune response depending on the inserted foreign genes than conventional vaccines using attenuated pathogenic microbes or viruses, whole cell absorbents for screening various peptides or antibodies, heavy metal elimination or waste water treatment, and whole cell bioconversion which can be continuously used without a decrease in catalytic activity by stably expressing an enzyme used in biological conversion on the cell surface.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A surface expression vector comprising a fragment of bclA gene encoding a fragment of *Bacillus anthracis* exosporium protein BclA as a cell surface anchoring motif, wherein the fragment of the bclA gene is selected from the group consisting of SEQ ID NO: 1, SEQ ID NO: 2, and SEQ ID NO: 3, and a gene encoding a promoter and a target protein, wherein the expression vector is constructed such that the target protein can be expressed in a form fused with the fragment of protein BclA on the cell surface when the gene encoding the target protein is expressed in a host cell.

2. The surface expression vector according to claim 1, wherein the promoter is tac promoter or any other inducible promoter.

3. The surface expression vector according to claim 1, wherein the target protein is a protein prepared by deleting a part of amino acid sequences of the target protein or subjecting to site-specific mutation in order to facilitate surface expression.

4. A transformed microorganism obtained by introducing the expression vector of claim 1 into a cell selected from the group consisting of Gram-positive bacteria, Gram-negative bacteria, *Actinomyces*, yeast and fungus.

5. The transformed microorganism according to claim 4, wherein the microorganism is mutated such that an intracellular or extracellular protease that degrades the expressed target protein cannot be produced, in order to facilitate surface expression of the target protein.

6. The transformed microorganism according to claim 5, wherein the microorganism is *Escherichia coli*.

7. A method for expressing a target protein on the surface of a cell, the method comprising the steps of: expressing the target protein on the cell surface by culturing the transformed microorganism of claim 4; and recovering the cell having the target protein expressed on the surface thereof.

8. The method according to claim 7, wherein the target protein is any one selected from the group consisting of hormones, hormone analogues, enzymes, enzyme inhibitors, signal transduction proteins or their fragments, antibodies or their fragments, single chain antibodies, binding proteins, binding domains, peptides, antigens, adherent proteins, structural proteins, regulatory proteins, toxin proteins, cytokines, transcription factors, blood coagulation factors, and plant defense-inducing proteins.

9. The method according to claim 8, wherein the target protein is streptavidin.

10. The method according to claim 8, wherein the enzyme is lipase.

11. A bioconversion method, the method is characterized by using the cells, prepared by the method of claim 8 and expressing the target protein having enzyme activity on the surface thereof.

12. A method for manufacturing a protein array, the method is characterized by attaching the cells, prepared by the method of claim 8 and expressing the target protein having enzyme activity on the surface thereof, on a substrate.

13. A method for producing an antibody in vertebrates, the method comprises:
    inducing an immune response by administering the cells, prepared by the method of claim 8 and expressing antigen on the surface thereof, to a vertebrate except a human being, and recovering the antibody produced by the immune response.

14. A method for preparing a chiral compound by carrying out optical resolution of racemic ester compounds using lipase, the method is characterized by using the lipase expressed on the surface of the cells prepared by the method of claim 10.

* * * * *